United States Patent
Sarstedt

[11] Patent Number: 6,006,931
[45] Date of Patent: Dec. 28, 1999

[54] MEMBRANE CAP FOR BLOOD-SAMPLING TUBE

[75] Inventor: Walter Sarstedt, Nümbrecht, Germany

[73] Assignee: Sarstedt AG & Co., Numbrecht, Germany

[21] Appl. No.: 09/149,956

[22] Filed: Sep. 9, 1998

[30] Foreign Application Priority Data

Sep. 9, 1997 [DE] Germany .............. 197 39 369

[51] Int. Cl.⁶ .................................................. B65D 41/20
[52] U.S. Cl. ................... 215/247; 215/363; 215/DIG. 3; 604/414; 604/415; 604/905
[58] Field of Search .................. 215/247, DIG. 3, 215/274, 275, 363, 355; 604/403, 411, 414, 415, 905, 533; 383/202

[56] References Cited

U.S. PATENT DOCUMENTS

| | | |
|---|---|---|
| 4,066,067 | 1/1978 | Micheli . |
| 4,204,606 | 5/1980 | Micheli . |
| 4,254,884 | 3/1981 | Maruyama ................ 215/247 X |
| 4,294,249 | 10/1981 | Sheehan et al. ............ 215/247 X |
| 4,592,092 | 5/1986 | McPhee .................... 215/DIG. 3 X |
| 4,892,222 | 1/1990 | Schmidt et al. ............ 215/247 X |
| 5,086,783 | 2/1992 | Macors . |
| 5,188,620 | 2/1993 | Jepson et al. .............. 604/415 X |
| 5,501,676 | 3/1996 | Niedospial et al. ......... 604/905 X |
| 5,853,094 | 12/1998 | Tanaka et al. .............. 215/247 |

*Primary Examiner*—Nathan Newhouse
*Attorney, Agent, or Firm*—Herbert Dubno; Andrew Wilford

[57] ABSTRACT

A cap for a blood-sampling tube has a collar adapted to fit on the tube and a tubular extension extending from the cap, defining an axis and having an outer end remote from the cap. An annular wall is formed inside the cap spaced from the outer end and an annular lip projects axially backward from the outer end and has an outer surface spaced radially inward of an inner surface of the extension and an axially directed inner end. A pierceable flat membrane in the extension on the annular wall snugly engages the inner surface of the extension and has an outer face spaced axially from the inner end of the lip. The lip has an inner surface defining a cylindrical passage of a predetermined diameter and the wall has an inner edge defining a similarly dimensioned coaxial annular passage.

3 Claims, 1 Drawing Sheet

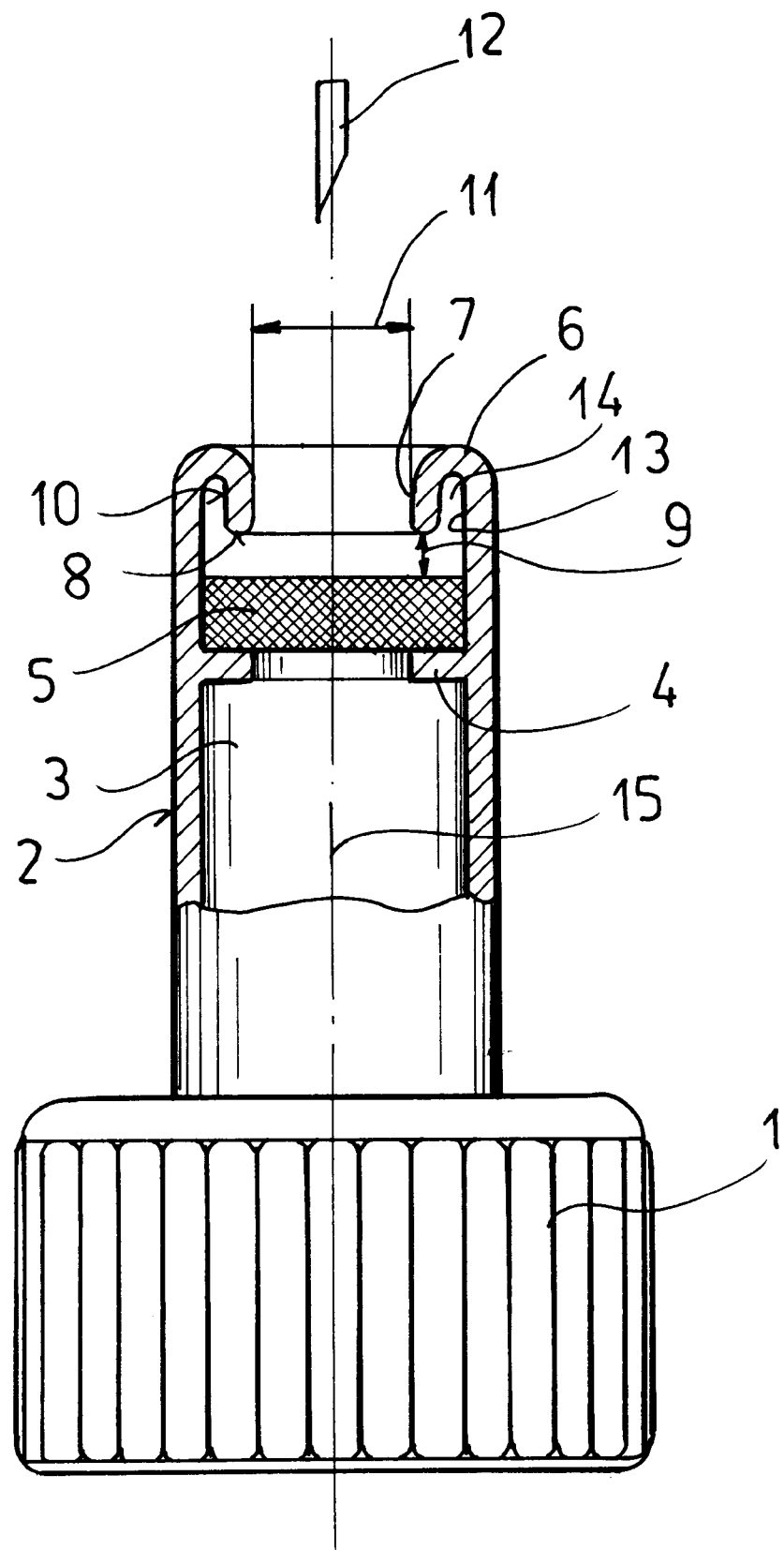

MEMBRANE CAP FOR BLOOD-SAMPLING TUBE

FIELD OF THE INVENTION

The present invention relates to a blood-sampling system. More particularly this invention concerns a membrane cap for a blood-sampling tube.

BACKGROUND OF THE INVENTION

As described in U.S. Pat. No. 4,378,812 a standard blood-collecting kit comprises a sampling tube or vial having an open end, a cap fitted over this end and having a pierceable membrane, and a needle holder that is in turn fitted to the cap. The needle assembly comprises a luer collar fitted with a double-ended cannula or needle whose front end is inserted through the patient's skin normally into a vein from which blood is to be drawn. The cap also has a luer fitting that fits complementary with the collar of the needle with the rear end of the needle poking through the membrane, and the opposite side of the cap is normally threaded to fit on the collection tube. When fully assembled with the front needle end inserted into a blood vessel, a piston in the collection tube is retracted to draw blood through the cannula into the tube. Once the tube is full, it can be unscrewed and another tube similarly filled, if desired.

When the holder is separated from the cap some blood often drips from the rear needle end onto the membrane. Since this membrane is invariably mounted at the extreme outer end or mouth of a tubular extension of the cap, this creates a substantial risk of contamination and provides a possibility of a medical worker coming into direct contact with the warm fresh blood thus dripped onto the exposed face of the membrane. In this day and age it is obvious that such a potentially dangerous situation must be avoided.

In order to eliminate this problem it has been suggested to provide the cap with a pierceable membrane or plug which is mounted at the outer end of the cap but that has an outwardly concavely recessed floor so that any drip does not simply lie on a flat end surface, but is slightly recessed. This type of plug reduces the already small diameter of the cap extension or the wall thickness of the extension is increased by the wall of the plug. This recess creates a reduction in the diameter of the cavity into which the needle is poked, which creates extra friction with the pierceable sterile sheath that normally surrounds the rear end of the needle and that is pushed back like a harmonica as the needle pierces it and the membrane of the cap. Furthermore when the needle assembly is pulled off the cap, any blood on the needle tip is transferred to the end of the bunched-up sheath and spread on the end of the cap. Furthermore if the blood tube is knocked over, any blood on the outside of the membrane is free to run out of the tube, once again creating a possibility of infection.

In order to avoid some of these difficulties it has been suggested to clamp the membrane rather forcibly in the cap. This reduces leakage and prevents it from being pulled out when the needle is extracted. On the other hand the extra compression of the elastomeric disk makes the membrane somewhat harder, requiring more force to be exerted to poke the needle through it, and causing the needle to exert more traction on it when being pulled out. Of course pulling the membrane out of the cap creates a serious problem of contamination and spoils the sample.

OBJECTS OF THE INVENTION

It is therefore an object of the present invention to provide an improved cap for a blood-sampling tube.

Another object is the provision of such an improved cap for a blood-sampling tube which overcomes the above-given disadvantages, that is which holds its membrane so that it is easily traversed by the needle, so that it cannot be pulled out of the cap, and so that any blood on its outside face will not get out of the cap even if it is laid horizontal.

SUMMARY OF THE INVENTION

A cap for a blood-sampling tube has according to the invention a collar adapted to fit on the tube and a tubular extension extending from the cap, defining an axis and having an outer end remote from the cap. An annular wall is formed inside the cap spaced from the outer end and an annular lip projects axially backward from the outer end and has an outer surface spaced radially inward of an inner surface of the extension and an axially directed inner end. A pierceable flat membrane in the extension on the annular wall snugly engages the inner surface of the extension and has an outer face spaced axially from the inner end of the lip.

The inverted lip serves to retain the membrane in place so that does not have to be a very tight fit. Thus it is not compacted and the needle can easily be poked through it. In addition the inverted lip forms according to the invention an axially inwardly open compartment or space so that any drop of blood that collects on the outer face of the recessed membrane will be trapped by this space if, for instance, the tube is knocked over.

Furthermore according to the invention the lip has an inner surface defining a cylindrical passage of a predetermined diameter and the wall has an inner edge defining a similarly dimensioned coaxial annular passage. Thus a needle that is poked into the outer end will not be likely to engage the membrane-supporting wall.

The lip and extension are unitarily formed and of the same wall thickness. Everything but the membrane is formed unitarily of plastic.

BRIEF DESCRIPTION OF TEE DRAWING

The above and other objects, features, and advantages will become more readily apparent from the following description, reference being made to the accompanying drawing whose sole FIGURE is a side view partly in axial section of a sample-tube cap according to the invention.

SPECIFIC DESCRIPTION

As seen in the drawing a sample-tube cap according to the invention has a standard threaded collar 1 adapted to be screwed onto the threaded neck of a blood-sample tube. This cap 1 has centered on an axis 15 a cylindrically tubular extension 2 forming an inner chamber 3 and formed internally with a radially inwardly projecting wall or ridge 4 on whose outer face sits a standard elastomeric and pierceable membrane 5 which is a snug fit against an inner wall 13 of the extension 2. An outer end 6 of the extension 2 is unitarily formed with an inverted and axially rearwardly extending lip 7 having an inner edge 8 axially spaced a distance 9 from an outer face of the membrane 5.

The folded-over lip 7 has an inner surface 10 spaced inward from the inner surface 13 of the extension 2 to form an axially inwardly open annular compartment or space 14 therewith. In addition the lip 7 defines a cylindrical passage having a diameter 11 equal to that of the inner edge of the membrane-supporting wall 4. Thus when a cannula or needle 12 is poked into the end of the extension 2, it will inherently be forced inward to pierce the membrane 5 at a location within the inner edge of the wall 4.

Presuming an unillustrated sample tube attached to the cap according to the invention has been filled and the needle 12 withdrawn, it is fairly common for a drop of potentially infectious blood to be left on the outside face of the membrane 5. Should the sample tube with the cap then be knocked over, this drop of blood will flow down and be trapped inside the space 14 so that it will not flow out of the cap. In addition the edge 8, which lies in a plane parallel to that of the outer face of the annular wall 4 and is spaced only a short distance much less than the thickness of the membrane 5 from the outer face of the membrane 5, prevents this membrane 5 from moving into a canted position in which leakage would be possible, even if the membrane 5 is shifted from its illustrated position by pulling the needle 12 out rapidly.

I claim:

1. A cap for a blood-sampling tube, the cap comprising:

a collar adapted to fit on the tube;

a tubular extension extending from the cap, defining an axis, and having an outer end remote from the cap;

an annular wall inside the cap spaced from the outer end;

an annular lip projecting axially backward from the outer end and having an outer surface spaced radially inward of an inner surface of the extension and an axially directed inner end; and a pierceable flat membrane in the extension on the annular wall, snugly engaging the inner surface of the extension, and having an outer face spaced axially from the inner end of the lip.

2. The sample-tube cap defined in claim 1 wherein the lip has an inner surface defining a cylindrical passage of a diameter and the wall has an inner edge defining a similarly dimensioned coaxial annular passage.

3. The sample-tube cap defined in claim 1 wherein the lip and extension are unitarily formed and of the same wall thickness.

\* \* \* \* \*